United States Patent
Hueffer et al.

(10) Patent No.: US 10,278,385 B2
(45) Date of Patent: May 7, 2019

(54) FORMULATIONS AND THEIR USE

(71) Applicants: Stephan Hueffer, Ludwigshafen (DE); Alejandra Garcia Marcos, Ludwigshafen (DE); Paul Klingelhoefer, Mannheim (DE); Gerhard Schnabel, Elsenfeld (DE)

(72) Inventors: Stephan Hueffer, Ludwigshafen (DE); Alejandra Garcia Marcos, Ludwigshafen (DE); Paul Klingelhoefer, Mannheim (DE); Gerhard Schnabel, Elsenfeld (DE)

(73) Assignee: BASF SE, Ludwigshafen (DE)

( * ) Notice: Subject to any disclaimer, the term of this patent is extended or adjusted under 35 U.S.C. 154(b) by 658 days.

(21) Appl. No.: 13/720,035

(22) Filed: Dec. 19, 2012

(65) Prior Publication Data
US 2013/0165321 A1  Jun. 27, 2013

Related U.S. Application Data

(60) Provisional application No. 61/578,243, filed on Dec. 21, 2011.

(51) Int. Cl.
*A01N 25/22* (2006.01)
*A01N 57/20* (2006.01)

(52) U.S. Cl.
CPC ............. *A01N 25/22* (2013.01); *A01N 57/20* (2013.01)

(58) Field of Classification Search
None
See application file for complete search history.

(56) References Cited

U.S. PATENT DOCUMENTS

| | | | |
|---|---|---|---|
| 5,703,015 A * | 12/1997 | Berger | A01N 25/30 504/206 |
| 5,948,421 A | 9/1999 | Okano et al. | |
| 2003/0181332 A1* | 9/2003 | Sedun et al. | 504/116.1 |
| 2006/0009360 A1 | 1/2006 | Pifer et al. | |

FOREIGN PATENT DOCUMENTS

| | | |
|---|---|---|
| CN | 1154060 A | 7/1997 |
| WO | WO 2007/030649 A2 | 3/2007 |

OTHER PUBLICATIONS

U.S. Appl. No. 13/533,083, filed Jun. 26, 2012, Stephan Hueffer, et al.
European Search Report dated May 10, 2012 in corresponding European Application No. 11 19 4743 (with an English Translation of Categories).
International Search Report dated May 27, 2013, in PCT/EP2012/074588.
Patrick J. Shea, et al., "Reversal of Cation-Induced Reduction in Glyphosate Activity with EDTA", Weed Science, vol. 32, XP-009168952, 1984, pp. 802-806.
Dorota Kolodynska, "Chelating Agents of a New Generation as an Alternative to Conventional Chelators for Heavy Metal Ions Removal from Different Waste Waters", Intechopen, XP-55060229, Sep. 22, 2011, pp. 339-370 plus cover page.
Office Action dated Jun. 25, 2015 issued in corresponding Chinese patent application No. 201280063420.3 (with partial English translation).

* cited by examiner

*Primary Examiner* — Monica A Shin
(74) *Attorney, Agent, or Firm* — Oblon, McClelland, Maier & Neustadt, L.L.P.

(57) ABSTRACT

The use of formulations comprising
(A) one or more aminocarboxylates, selected from among methylglycine diacetate (MGDA) and its alkali metal salts, glutamic acid diacetate (GLDA) and its alkali metal salts, iminodisuccinate, hydroxyethylimine diacetate and ethyleneiminodisuccinate and the corresponding alkali metal salts,
(B) at least one organic compound selected from among organic phosphates, organic phosphonates and organic phosphites and salts of the abovementioned organic compounds, and
(C) optionally water,
for application to plants or the ground.

13 Claims, No Drawings

FORMULATIONS AND THEIR USE

The present invention relates to the use of formulations comprising (A) one or more aminocarboxylates, selected from among methylglycine diacetate (MGDA) and its alkali metal salts, glutamic acid diacetate (GLDA) and its alkali metal salts, iminodisuccinate, hydroxyethylimine diacetate and ethyleneiminodisuccinate and the corresponding alkali metal salts, (B) at least one organic compound selected from among organic phosphates, organic phosphonates and organic phosphites and salts of the abovementioned organic compounds, and (C) optionally water, for application to plants or the ground.

Furthermore, the present invention relates to formulations comprising (A) one or more aminocarboxylates, selected from among methylglycine diacetate (MGDA) and its alkali metal salts, glutamic acid diacetate (GLDA) and its alkali metal salts, iminodisuccinate, hydroxyethylimine diacetate and ethyleneiminodisuccinate and the corresponding alkali metal salts, (B) at least one organic compound selected from among organic phosphates, organic phosphonates and organic phosphites and salts of the abovementioned organic compounds, and (C) optionally water.

Furthermore, the present invention relates to a process for the preparation of the formulations according to the invention.

It has long been desired to improve the yields of soils as regards fertility. In this context, it is not only the fertilization of the soil which plays a role, but also the control of undesired plants and animals capable of reducing a crop yield.

A variety of organic phosphorus-comprising compounds, for example organic phosphates, organic phosphonates and organic phosphites and salts of the abovementioned organic compounds, have a range of effects on organisms such as weeds, vermin and undesired fungi. A problem when applying many of these organic compounds is that they are capable of reacting with soil components such as iron oxides, aluminum oxides, layer silicates, calcium compounds and magnesium compounds and/or are capable of being adsorbed by the former, whereby they are converted into a form which is insoluble in water and hence no longer available to plants. This process is also referred to as mineralization. Depending on the soil composition, mineralization takes place within a period of 2 to 14 days. Therefore, the activity is unsatisfactory despite the fact that the quantity available of organic phosphorus compounds is high or indeed too high. At the same time, the amount of active substances stored in the soil and the environment is constantly being increased according to current practice, which is likewise undesired.

A similar problem is that a mineralization of organic phosphorus-comprising compounds may also be caused by the alkaline-earth metal ions which may be present in the water used for making dilute spray mixture. Depending on the water hardness and the degree of dilution, significant amounts of active substance may be eliminated in this manner.

In many cases, therefore, glyphosate is applied to the soil together with considerable amounts of ammonium sulfate. In this context, the amounts of ammonium sulfate may be considerable. Thus, EP 0 290 416 discloses a typical concentrate 74 g/l glyphosate (free acid), 49 g/l glyphosate monoisopropylammonium salt, 120 g/l fatty amine ethoxylate and 280 g/l ammonium sulfate. Between 100 and 600 liters of formulation are typically employed per ha of field. This corresponds to an active substance discharge of 1-6 kg/ha field. The formulation comprises more ammonium sulfate than active substance.

It was therefore an object to provide formulations whose organic phosphorus compounds can be taken up readily by the soil or plants, for example in such a manner that an absorption capacity over a period of up to 8 weeks is ensured. It was therefore an object to provide uses of formulations by means of which organic phosphorus compounds can be taken up readily by soils and in particular plants. It is furthermore an object to provide a method by means of which the organic phosphorus compounds can be made readily bioavailable.

Accordingly, there have been found the uses and formulations defined at the outset.

According to the invention, there is used as least one formulation comprising (A) one or more aminocarboxylates, also termed aminocarboxylate (A) for short or else, summarily, compound (A), selected from among methylglycine diacetate (MGDA) and its alkali metal salts, glutamic acid diacetate (GLDA) and its alkali metal salts, iminodisuccinate, hydroxyethylimine diacetate and ethyleneiminodisuccinate and the corresponding alkali metal salts (B) at least one organic compound, also termed compound (B), selected from among organic phosphates, organic phosphonates and organic phosphites and salts of the abovementioned organic compounds, and (C) optionally water, for application to plants or the ground.

Compound (A) may be present as the free acid or preferably in partially or fully neutralized form, in other words as a salt. Counterions which may be selected are, for example, inorganic cations, for example ammonium or alkali, preferably $Na^+$, $K^+$, or organic cations, preferably ammonium which is substituted by one or more organic residues, in particular mono-$C_1$-$C_4$-alkylammonium, for example isopropylammonium, furthermore triethanolammonium, N,N-diethanolammonium, N-mono-$C_1$-$C_4$-alkyldiethanolammonium, for example N-methyldiethanolammonium or N-n-butyldiethanolammonium, and N,N-di-$C_1$-$C_4$-alkylethanolammonium. Alkali metal ions are preferred, $Na^+$ and $K^+$ especially preferred.

For the purposes of the present invention, aminocarboxylates (A) are understood as meaning those organic compounds which include a tertiary amino group which includes one or two $CH_2$—COOH which group(s) can be partially or fully neutralized, as mentioned above.

In another embodiment of the present invention, aminocarboxylates (A) are selected from among those organic compounds which include a secondary amino group which includes one or two CH(COOH)$CH_2$—COOH which group(s) can be partially or fully neutralized, as mentioned above.

In one embodiment of the present invention, aminocarboxylates (A) are selected from among iminodisuccinate (IDS) and hydroxyethyliminedisuccinate (HEIDS) and also the corresponding alkali metal salts. In another embodiment of the present invention, aminocarboxylates (A) are selected among hydroxyethyliminediacetate (HEIDA) and also the corresponding alkali metal salts.

Preferred aminocarboxylates (A) and polyaminocarboxylates (A) are those organic compounds whose structure is based on an amino acid whose amino group(s) include(s) one or two $CH_2$—COOH groups and which are tertiary amino groups. In this context, amino acids may be selected among L-amino acids, R-amino acids and enantiomer mixtures of amino acids, for example the racemates.

In one embodiment of the present invention, compound (A) is selected among methylglycine diacetate (MGDA) and glutamic diacetate (GLDA) and their derivates and preferably their salts, in particular their sodium and potassium salts. Very especially preferred are methylglycine diacetate and the trisodium salt of MGDA.

Compound (B) is selected from among organic phosphates, organic phosphonates and organic phosphites and salts of the abovementioned organic compounds. Preferred compounds (B) are organic phosphonates.

For the purposes of the present invention, organic phosphates are defined as compounds which correspond to the general formula (I)

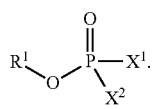

(I)

In this formula, the variables are defined as follows:

$R^1$ is selected from among $C_1$-$C_{20}$-alkyl, $C_3$-$C_{10}$-cycloalkyl or $C_6$-$C_{14}$-aryl, unsubstituted or at least monosubstituted by $C_1$-$C_6$-alkyl, phenyl, OH, $OR^2$, $NH_2$, $NHR^2$, $N(R^2)_2$, SH, $SR^2$, $CH_2OH$, $CH_2OR^2$, $CH_2NH_2$, $CH_2NHR^2$, $CH_2N(R^2)_2$, $CH_2SH$, $CH_2SR^2$, $CH_2C_6H_5$, $CH_2$—COOH, $CH_2COOM^1$, $(CH_2)_2$—COOH, $(CH_2)_2COOM^1$, $CH_2$—$NH_2(+)$—$CH_2COOH$, $CH_2$—$NH_2(+)$-$CH_2COOM^1$, $(CH_2)_2$—$NH_2(+)$—$CH_2COOH$, $(CH_2)_2$—$NH_2(+)$-$CH_2COOM^1$, $CH_2$—NH—$CH_2COOH$, $CH_2$—NH-$CH_2COOM^1$, $(CH_2)_2$—NH—$CH_2COOH$, $(CH_2)_2$—NH-$CH_2COOM^1$;

it being possible for at least one C atom in $C_1$-$C_{20}$-alkyl or $C_3$-$C_{10}$-cycloalkyl to be replaced by oxygen, NH, $NR^2$ or sulfur, $R^2$ is $C_1$-$C_6$-alkyl, phenyl, benzyl, $CH_2OH$, $CH_2OR^2$, $CH_2NH_2$, $CH_2NHR^2$, $CH_2N(R^2)_2$, $CH_2SH$, $CH_2SR^2$, $X^1$ is selected from among OH and $OM^1$, where $M^1$ is selected from among alkali metal cations, for example $Na^+$, $K^+$, furthermore alkaline-earth metal cations, for example $Mg^{2+}$, and ammonium ions, unsubstituted or mono- or polysubstituted by $C_1$-$C_4$-alkyl or $CH_2CH_2OH$. Examples of substituted ammonium ions are $CH_3NH_3^+$, $(CH_3)_2NH_2^+$, $(CH_3)_3NH^+$, $(CH_3)_4N^+$, $CH_3CH_2NH_3^+$, $(C_2H_5)_2NH_2^+$, $(C_2H_5)_3NH^+$, $(C_2H_5)_4N^+$, $(CH_3)_2CHNH_3^+$, $(CH_3)_2CHNH(CH_3)^{2+}$, $(CH_3)_2CHNH_2(CH_3)^+$, $CH_3NH(CH_2CH_2OH)_2^+$, $(CH_3)_2NH(CH_2CH_2OH)^+$, $X^2$ is selected from among OH, $OM^1$ and $OR^1$, where two $R^1$ or $M^1$ may be identical or different.

For the purposes of the present invention, organic phosphites are defined as compounds which correspond to general formula (II)

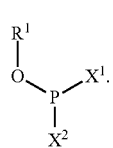

(II)

In this context, the variables are as defined hereinabove.

Compound (B) is preferably selected from organic phosphonates. For the purposes of the present invention, organic phosphonates are defined as compounds which correspond to the general formula (III)

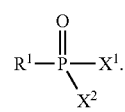

(III)

In this context, the variables are as defined hereinabove.

In one embodiment of the present invention, compound (B) is selected from among herbicides, in particular those with activity against monocotyledonous or dicotyledonous weeds. Especially preferred are herbicides with activity against monocotyledonous and dicotyledonous weeds.

In one embodiment of the present invention, compound (B) is selected from among glyphosate and salts of glyphosate, for example salts with cations $M^1$. Especially preferred cations are $K^+$, the ammonium and the isopropylammonium ion. In this context, glyphosate may be present in partially or fully neutralized form.

In one embodiment of the present invention, compound (B) is selected from among monoisopropylammonium glyphosate.

In accordance with the invention, one uses formulations which may comprise water (C). Formulations according to the invention may comprise water (C). Water may be present for example in amounts of from 0.1 to 10% by weight, based on the total formulation according to the invention, or the total formulation used in accordance with the invention. In another embodiment, a formulation according to the invention, or a formulation used in accordance with the invention, comprises more than 10, but up to 95%, of water. In another embodiment of the present invention, a formulation according to the invention, or formulation used in accordance with the invention, comprises water (C) in the range of from 95.01 to 99.9% by weight.

Formulations according to the invention may be present as a powder, as moist powder, a suspension, as powder slurry or a solution. Formulations according to the invention may, for example, be concentrates or spray solutions.

To employ formulations according to the invention, they can be applied to plants or to the ground or to growth substrates, for example as an active substance formulation or in combination with a fertilizer. To that end, the formulation according to the invention can be applied manually or mechanically to soil or growth substrate which is bare or sustains vegetation, or formulation according to the invention can be applied manually or mechanically to plants.

Examples of suitable plants are vegetables, grasses, cereals, trees, root crops, bushes, shrubs and flowers. Especially preferred are oilseed rape, wheat, millet/sorghum, rye, barley, avocado, citrus fruit, mango, coffee, deciduous tree crops, grapes and other soft fruit plants, beans, in particular soybeans, furthermore maize, tomatoes, cucumbers, in particular zucchini and salad cucumbers, pumpkins, furthermore lettuce, potatoes, fodder beet, sugar beet, paprika, sugarcane, hops, tobacco, pineapple, palms, in particular coconut palms, furthermore rubber trees including Brazilian rubber trees (Hevea brasiliensis), and ornamental plants, in particular roses, dahlias, tulips, narcissus, daffodils, carnations and chrysanthemums.

For application purposes, the formulation according to the invention can be applied over an area to be treated, for example by aircraft or vehicle, or it can be applied with the aid of an irrigation system. Other types of application are spraying and root dosage, liquid or solid.

In one embodiment of the present use, at least one formulation is used in accordance with the invention, which formulation comprises at least one organic compound (D) selected from among urea and citric acid and its alkali metal salts. Preferred alkali metal salts of citric acid are tripotassium citrate ("potassium citrate") and the trisodium salt of citric acid ("sodium citrate").

In one embodiment, one will use, according to the invention, at least one formulation which comprises at least one inorganic compound (E). Preferred inorganic compounds (E) are ammonium salts of mineral acids, in particular ammonium sulfate.

In one embodiment of the present invention, one will use, in accordance with the invention, at least one formulation which comprises at least one additive (F) selected from among wetters, surfactants, spray adjuvants and spreaders. Especially suitable additives (F) are surfactants, for example $C_8$-$C_{20}$-alkyl sulfates, $C_8$-$C_{20}$-alkylsulfonates and $C_6$-$C_{20}$-alkyl ether sulfates having one to 6 ethylene oxide units per molecule. Further suitable surfactants are nonionic surfactants such as, for example, alkylpolyglucosides and $C_6$-$C_{20}$-alkylaminoalkoxylates having, for example, 2 to 30 alkoxylate units per mole, preferably $C_6$-$C_{20}$-alkylaminoethoxylates having for example 2 to 30 ethylene oxide units per mole, and in particular tallow fatty amine ethoxylates having 10 to 20 ethylene oxide units per mole.

In one embodiment of the present invention, at least one formulation comprising at least one polyaminocarboxylate is used in accordance with the invention.

For the purposes of the present invention, polyaminocarboxylates (A) are understood as meaning those organic compounds which include at least two tertiary amino groups which, independently of one another, include in each case one or two $CH_2$—COOH which group(s) can be partially or fully neutralized, preferably using alkali metal, more preferably using $Na^+$ or $K^+$.

In another embodiment of the present invention, polyaminocarboxylates (A) are selected from among those organic compounds which include at least two secondary amino groups, each of which includes one CH(COOH) $CH_2$—COOH which group(s) can be partially or fully neutralized, as mentioned above.

Preferred polyaminocarboxylates (A) are selected among 1,2-diaminoethanetetraacetic acid (EDTA), ethylenediaminedisuccinate (EDDS), tetraacetylmethylenediamine, tetraacetylhexylenediamine, diethylenetriaminepentaacetate (DTPA), hydroxyethylenediaminetriacetate (HEDTA) and their respective salts, in particular alkali metal salts, very especially preferably the sodium salts and potassium salts, and mixed sodium potassium salts.

The present invention furthermore relates to formulations comprising
(A) one or more aminocarboxylates, selected from among methylglycine diacetate (MGDA) and its alkali metal salts, glutamic acid diacetate (GLDA) and its alkali metal salts, iminodisuccinate, hydroxyethylimine diacetate and ethyleneiminodisuccinate and the corresponding alkali metal salts,
(B) at least one compound (B) selected from among herbicides which are selected from among organic phosphates, organic phosphonates and organic phosphites and salts of the abovementioned organic compounds, and
(C) optionally water.

Aminocarboxylates (A), polyaminocarboxylates and compounds (B) are described hereinabove.

In one embodiment of the present invention, formulation according to the invention comprises at least one aminocarboxylate (A) and at least one polyaminocarboxylate.

In one embodiment of the present invention, compound (B) is selected from among herbicides with activity against monocotyledonous or dicotyledonous weeds. Especially preferred are herbicides with activity against monocotyledonous and dicotyledonous weeds.

Compound (B) is selected from among organic phosphates, organic phosphonates and organic phosphites and salts of the abovementioned organic compounds.

It is especially preferred to select compound (B) from among glyphosate and salts of glyphosate, in particular monoisopropylammonium glyphosate.

In one embodiment of the present invention, formulation according to the invention comprises: in total in the range of from 1 to 90% by weight, preferably 10 to 50% by weight, of aminocarboxylate (A) and polyaminocarboxylate (A), where either the content of aminocarboxylate (A) or the content of polyaminocarboxylate (A) may be zero, and in total in the range of from 0.1 to 25% by weight, preferably 0.25 to 5% by weight, of compound (B).

In the context, % by weight refer in each case to the solids content of formulation according to the invention.

Formulation according to the invention may furthermore comprise water (C)

In one embodiment of the present invention, formulation according to the invention comprises at least one further substance selected from among
(D) organic compounds which are selected from among urea and citric acid and its alkali metal salts,
(E) inorganic substances, preferably ammonium salts of mineral acids, in particular ammonium sulfate,
(F) additives, selected from among wetters, surfactants, spreaders and spray adjuvants.

Organic compounds (D), inorganic substances (E), polyaminocarboxylates and additives (F) are described hereinabove.

Especially suitable additives (F) are surfactants, for example $C_8$-$C_{20}$-alkyl sulfates, $C_8$-$C_{20}$-alkylsulfonates and $C_8$-$C_{20}$-alkyl ether sulfates having one to 6 ethylene oxide units per molecule. Further suitable surfactants are nonionic surfactants such as, for example, alkylpolyglucosides and $C_6$-$C_{20}$-alkylaminoalkoxylates, preferably $C_6$-$C_{20}$-alkylaminoethoxylates, and in particular tallow fatty amine ethoxylates.

In one embodiment of the present invention, formulation according to the invention comprises
in total in the range of from zero to 25% by weight, preferably 1 to 10% by weight, of organic compound(s) (D),
in total in the range of from zero to 5% by weight, preferably 0.1 to 2.5% by weight, of inorganic substance(s) (E),
in total in the range of from zero to 25% by weight, preferably 1 to 15% by weight, of additive(s) (F), in the range of from zero to 10% by weight of polyaminocarboxylate.

In this context, % by weight refer in each case to the solids content of formulation according to the invention.

In one embodiment of the present invention, formulation according to the invention has a pH in the range of from 4 to 11, preferably from 5 to 9. In a specific variant, formulation according to the invention has a pH in the range of from 9 to 11.

Formulations according to the invention can be used particularly advantageously for efficiently improving the herbicidal activity of organic compounds (B) on useful plants without applying large amounts of undesirable compounds or without large amounts of undesirable compounds reaching the ground water, and which would lead to a general pollution or inland watercourses and/or without accumulation via the food chain. Especially advantageous is the use of formulations according to the invention in environments with frequent precipitation, in which organic compounds (B), even when applied analogously to foliar fertilization, are washed into the ground to a considerable extent, but, when using formulation according to the invention, no longer become ineffective in the soil as the result of mineralization.

A further subject matter of the present invention is a process for the preparation of formulations according to the invention, also referred to as preparation process according to the invention within the scope of the present invention.

In one embodiment of the preparation process according to the invention, a procedure is followed in which:
  (A) one or more aminocarboxylate(s) (A), selected from among methylglycine diacetate (MGDA) and its alkali metal salts, glutamic acid diacetate (GLDA) and its alkali metal salts, iminodisuccinate, hydroxyethylimine diacetate and ethyleneiminodisuccinate and the corresponding alkali metal salts, and
  (B) at least one organic compound selected from among herbicides which are selected from organic phosphates, organic phosphites and organic phosphonates and salts of the abovementioned compounds,
are mixed with each other in the presence of water (C) and optionally all or some of the water (C) is removed.

In one embodiment of the present invention, at least one compound (A) and at least one compound (B) are dissolved in water (C), for example in 10% by volume up to the 10-fold amount (based on volume), based on the total of compound (A) and inorganic compound (B). Thereafter, all or some of the water (C) may be removed.

In another embodiment of the present invention, at least one compound (B) is suspended in a solution of at least one compound (A) in water (C), for example in 10% by volume up to the 10-fold amount (based on volume), based on the total of compound (A) and compound (B). Thereafter, all or some of the water (C) may be removed.

In another embodiment of the preparation process according to the invention, a procedure is followed in which, in the presence of water (C) and
  (A) one or more aminocarboxylate(s) (A), selected from among methylglycine diacetate (MGDA) and its alkali metal salts, glutamic acid diacetate (GLDA) and its alkali metal salts, iminodisuccinate, hydroxyethylimine diacetate and ethyleneiminodisuccinate and the corresponding alkali metal salts or
  (B) at least one compound, preferably at least two compounds (B), in each case selected from among herbicides which are selected from among organic phosphates, organic phosphites and organic phosphonates and salts of the abovementioned compounds,
is prepared in the presence of at least one inorganic substance (E) and
optionally all or some of the water (C) is removed.

It is therefore possible for example to use potassium hydroxide as the inorganic substance (E) and thereby to prepare the potassium salt of compound (B) in situ.

It is preferred to select one or more ammonium salts of mineral acids as the inorganic substance (E), in particular ammonium sulfate.

In another variant, potassium hydroxide is employed as inorganic substance (E) and is mixed in the presence of water (C) with aminocarboxylate(s) (A) or polyaminocarboxylate(s) as the free acid(s), whereby potassium salts of aminocarboxylate(s) (A) or polyaminocarboxylate(s) are prepared.

Optionally, and in each case before or after removal of the water (C), a mixture may be made in addition with at least one further substance selected from among
  (D) organic compounds which are selected from among urea and citric acid and its alkali metal salts,
  (E) inorganic substances, in particular ammonium sulfate, and
  (F) additives selected from among wetters, surfactants, spreaders and spray adjuvants or with at least one polyaminocarboxylate.

In another embodiment, a mixture may be made in addition with at least one further substance selected from among
  (D) organic compounds which are selected from among urea and citric acid and its alkali metal salts,
  (E) inorganic substances, in particular ammonium sulfate, and
  (F) additives selected from among wetters, surfactants, spreaders and spray adjuvants, or with at least one polyaminocarboxylate without removing the water (C).

In one embodiment of the preparation process according to the invention, a procedure is followed in which all or, preferably, some of the water (C) is removed, for example by evaporation, distillation, freeze-drying, in particular by spray-drying or spray granulation. In another embodiment, the water employed during the preparation according to the invention remains in the formulation according to the invention.

A further subject matter of the present invention is a method of fertilizing plants, wherein at least one formulation according to the invention is applied mechanically or manually to ground and/or plants.

Formulations according to the invention can be stored and transported particularly readily. Therefore, a further subject matter of the present invention is a method of storing compounds (B), wherein the compounds (B) are stored in the form of the formulation according to the invention. Therefore, a further subject matter of the present invention is a method of transporting compounds (B), wherein the compounds (B) are stored in the form of the formulation according to the invention.

In the context of the present invention, storing is understood as meaning that compounds (B) are retained over a period of at least one day without performing a chemical reaction on compound (B).

In the context of the present invention, transporting is understood as meaning that compound (B) is conveyed over a certain distance with the aid of a conveyance means outside a chemical production plant, for example at least 100 m, preferably 1 km to 10 000 km. Suitable conveyance means are railway cars, trucks, ships and aeroplanes.

Storage in accordance with the invention may be performed in storage containers of any size, for example in silos, bins, cellars and tanks made of plastic (IBC) or of metal. The fill level of the container is from 1-100% by volume and the dilution may be chosen as desired up to 10 000/1.

In accordance with the invention storage may be effected for example for at least one day, with at least two days up to one year being preferred.

Transporting in accordance with the invention may be effected over a period of from 1 to 10 days.

For example, storage or transporting according to the invention may be effected at a temperature in the range from zero to 60° C., but the temperature may also exceed or be below this value. For example, storage or transporting in accordance with the invention may also be effected under freezing conditions, for example at −70 to −0.5° C.

The invention is illustrated by working examples.

All % are % by weight unless expressly stated otherwise.

EXAMPLES

I. Preparation of Concentrates

I.1 Preparation of Comparative Concentrate V-K.1

275 g of ammonium sulfate (E.1) were dissolved in 400 g of water. Thereafter, 70 g of glyphosate (free acid) (B.1) and 56 g of glyphosate monoisopropylammonium salt (B.2) were added. Thereafter, water was added to a total weight of 1000 g. This gave comparative concentrate V-K.1.

I.2 Preparation of Formulation K.2 According to the Invention 70 g of glyphosate (free acid) (B.1) and 56 g of glyphosate monoisopropylammonium salt (B.2) were dissolved in 620 g of a 40% by weight strength aqueous solution of methylglycinediacetate trisodium salt (A.1). Thereafter, water was added to a total of 1000 g. This gave formulation K.2 according to the invention.

I.3 Preparation of Formulation K.3 According to the Invention 70 g of glyphosate (free acid) (B.1) and 56 g of glyphosate monoisopropylammonium salt (B.2) were dissolved in 710 g of a 40% by weight strength aqueous solution of methylglycinediacetate tripotassium salt (A.2). Thereafter, water was added to a total of 1000 g. This gave formulation K.3 according to the invention.

I.4 Preparation of Formulation K.4 According to the Invention 70 g of glyphosate (free acid) (B.1) and 56 g of glyphosate monoisopropylammonium salt (B.2) were dissolved in 710 g of a 40% by weight strength aqueous solution of methylglycinediacetate trisodium salt (A.1). Thereafter, 120 g of ammonium sulfate (E.1) were added. Thereafter, water was added to a total of 1000 g. This gave formulation K.4 according to the invention.

I.5 Preparation of Formulation K.5 According to the Invention 70 g of glyphosate (free acid) (B.1) and 56 g of glyphosate monoisopropylammonium salt (B.2) were dissolved in 670 g of a 40% by weight strength aqueous solution of glutamic acid diacetate trisodium salt (A.3). Thereafter, water was added to a total of 1000 g. This gave formulation K.5 according to the invention.

I.6 Preparation of Comparative Concentrate V-K.6

275 g of ammonium sulfate (E.1) were dissolved in 400 g of water. Thereafter, 70 g of glyphosate (free acid) (B.1) and 56 g of glyphosate monoisopropylammonium salt (B.2) were added. Thereafter, 120 g of ethoxylated tallow fatty amine (15 ethylene oxide units per mole) were added. Thereafter, water was added to a total weight of 1000 g. This gave comparative concentrate V-K.6.

I.7 Preparation of Formulation K.7 According to the Invention 70 g of glyphosate (free acid) (B.1) and 56 g of glyphosate monoisopropylammonium salt (B.2) were dissolved in 620 g of a 40% by weight strength aqueous solution of methylglycinediacetate trisodium salt (A.1). Thereafter, 120 g of ethoxylated tallow fatty amine (15 ethylene oxide units per mole) were added. Thereafter, water was added to a total weight of 1000 g. This gave formulation K.7 according to the invention.

I.8 Preparation of Formulation K.8 According to the Invention 70 g of glyphosate (free acid) (B.1) and 56 g of glyphosate monoisopropylammonium salt (B.2) were dissolved in 710 g of a 40% by weight strength aqueous solution of methylglycinediacetate tripotassium salt (A.2). Thereafter, 120 g of ethoxylated tallow fatty amine (15 ethylene oxide units per mole) were added. Thereafter, water was added to a total weight of 1000 g. This gave formulation K.8 according to the invention.

I.9 Preparation of Formulation K.9 According to the Invention 70 g of glyphosate (free acid) (B.1) and 56 g of glyphosate monoisopropylammonium salt (B.2) were dissolved in 730 g of a 40% by weight strength aqueous solution of glutamic acid diacetate trisodium salt (A.3). Thereafter, 120 g of ethoxylated tallow fatty amine (15 ethylene oxide units per mole) were added. Thereafter, water was added to a total weight of 1000 g. This gave formulation K.9 according to the invention.

I.10 Preparation of Formulation K.10 According to the Invention 20 g of glyphosate (free acid) (B.1) and 14 g of glyphosate monoisopropylammonium salt (B.2) were dissolved in 510 g of a 40% by weight strength aqueous solution of methylglycinediacetate tripotassium salt (A.2). Thereafter, 90 g of ethoxylated tallow fatty amine (15 ethylene oxide units per mole) were added. Thereafter, water was added to a total weight of 1000 g. This gave formulation K.10 according to the invention.

I.11 Preparation of Spray Solutions (General Protocols)

I.11.1 Preparation of Spray Solutions I 50 g of a formulation K.2 according to the invention were diluted with water (water hardness 110 ppm) to 1000 g (1/20). This gave spray solution SL.2 according to the invention.

An analogous procedure was followed with comparative concentrate V-K.1 and with the formulations K.3 to K.5 according to the invention. This gave comparative spray solution V-SL.1 and the spray solutions SL.3 to SL.5 according to the invention, respectively.

I.11.2 Preparation of Spray Solutions II 1 g of a formulation K.7 according to the invention were diluted with water (water hardness 110 ppm) to 1000 g (1/1000). This gave spray solution SL.7 according to the invention.

An analogous procedure was followed with comparative concentrate V-K.6 and with the formulations K.5 to K.10 according to the invention. This gave comparative spray solution V-SL.6 and the spray solutions SL.8 to SL.10 according to the invention, respectively.

II. Studies on Soil Segments

II.1 Mineralization Experiments, General Protocol Following the Example SL.2

1 kg of loose sediment of ground earth from South Germany with a water content of 23%, a pH of 6.1-6.3 and a mineral fraction of 45% (composition of the mineral fraction: 38% quartz, 20% carbonates, 20% mica, 9% clay mineral, 7% feldspar, 3% iron oxide; with an Al content of 1.7%, a Ca content of 1.4%, an Fe content of 2.1%, a phosphate content (determined as $P_2O_5$) of 240 mg $P_2O_5$/kg soil) were placed in a round vessel (diameter 12 cm).

The soil was sprayed with 240 ml of spray solution SL.2 according to the invention, using a diffuser, diffusing, over a period of 48 hours, in each case 30 ml of the spray solution SL.2 according to the invention over the surface of the brown earth every 6 hours. Thereafter, the soil was stored for a further 72 h at 20° C. without covering the vessels.

For the analysis, the soil was subsequently transferred into a 2-liter vessel and made into a slurry with 1 liter of water at 20° C. The mixture was stirred for 20 minutes and the soils were separated from the filtrate using a suction filter. Slurrying and filtration were repeated twice. The water of the collected filtrates were stripped off in a rotary evaporator. The residue was analyzed for the glyphosate content (HPLC).

Thus the dosage of glyphosate, based on the acid, amounted to 1340 mg. The amount of eluted glyphosate and the amount of mineralized glyphosate fixed in the soil were calculated accordingly.

An analogous procedure was followed for studying the comparative spray solution V-SL.1 and the comparative spray solutions SL.3 to SL.5. The results are compiled in Table 1.

TABLE 1

Studies of soil samples

| | V-SL.1 | SL.2 | SL.3 | SL.4 | SL.5 |
|---|---|---|---|---|---|
| Mineralized glyphosate [mg] | 1236 | 410 | 250 | 246 | 700 |
| Mineralized glyphosate [%] | 92.2 | 30.6 | 18.7 | 18.4 | 52.2 |
| Eluted glyphosate [mg] | 104 | 930 | 1090 | 1094 | 640 |

II.2 Long-Term Mineralization Experiments as a Function of the Sample Depths, Protocol Following the Example SL.7

In a further experiment, agricultural soil (loose-sediment brown earth) in roof-covered plots in each case 1 m² in size were treated with spray solutions II over a period of 60 days. The depth of the loose-sediment brown earth strata was 90 cm.

A plot was treated with in each case a total of 10 liters of SL.7/m² over a period of 8 weeks and artificially irrigated with 50 liters of water/m² (water hardness <10 ppm). To this end, the plot was sprayed every 3 days with 0.5 liters of SL.7 followed by irrigation for 6 hours with 2.5 l water (water hardness <10 ppm). After the treatment, which lasted for 8 weeks, irrigation was continued for a further 8 weeks without applying other substances (3 liters/m² every 3 days).

Thereafter, cores down to a depth of 80 cm were sampled using an auger (diameter 10 cm). 4 cores were removed to obtain representative means for the subsequent studies. The cores were divided into disks with a thickness of 10 cm. The amount of the glyphosate fraction which could be eluted with water was determined for these disks, using in each case a procedure as described in II.1.

TABLE 2

Studies of soil samples in long-term experiments

| | V-SL.6 | SL.7 | SL.8 | SL.9 | SL.10 |
|---|---|---|---|---|---|
| [mg] eluted glyphosate depth 0-10 cm | 82 | 360 | 393 | 387 | 93 |
| [mg] eluted glyphosate depth 10-20 cm | 22 | 290 | 301 | 279 | 26 |
| [mg] eluted glyphosate depth 20-30 cm | 9 | 47 | 49 | 39 | 7 |
| [mg] eluted glyphosate depth 40-50 cm | — | 15 | 15 | 12 | — |
| [mg] eluted glyphosate depth 60-70 cm | — | 4 | 3 | — | — |
| [mg] eluted glyphosate depth 70-80 cm | — | — | — | — | — |

The experimental findings demonstrate that the availability of glyphosate by the addition of aminocarboxylates (A) is at a high level despite a certain water hardness (spray solution) and despite the presence of soil minerals. Even SL.10, which comprises only 26% of the glyphosate fraction, compared with V-SL.6, outperformed V-SL.6, in respect of the elutable glyphosate fraction.

We claim:

1. A formulation, comprising:
   (A) at least one aminocarboxylate selected from the group consisting of an alkali metal salt of MGDA and an alkali metal salt of GLDA;
   (B) at least one organic compound selected from the group consisting of glyphosate and glyphosate monoisopropylammonium salt; and
   (C) optionally water.

2. The formulation according to claim 1, further comprising a polyaminocarboxylate.

3. The formulation according to claim 1, wherein the aminocarboxylate (A) is an alkali metal salt of MGDA.

4. The formulation according to claim 1, wherein the aminocarboxylate (A) is an alkali metal salt of GLDA.

5. The formulation according to claim 1, wherein a solids content weight ratio of the aminocarboxylate (A) to the organic compound (B) is in a range of 1.97:1 to 6.00:1.

6. The formulation according to claim 1, wherein a solids content weight ratio of the aminocarboxylate (A) to the organic compound (B) is in a range of 1.97:1 to 2.32:1.

7. The formulation according to claim 5, further comprising an ethoxylated tallow fatty amine.

8. The formulation according to claim 5, wherein application of the formulation to soil results in less mineralization of the glyphosate than does application of a formulation comprising the same amount of glyphosate but comprising ammonium sulfate instead of the aminocarboxylate.

9. A method, comprising:
   applying the formulation of claim 1 to a plant or the ground.

10. The method according to claim 9, wherein the formulation further comprises a wetter.

11. The method according to claim 9,
wherein the formulation comprises water.

12. A method of growing a plant, the method comprising:
treating a ground or the plant at least once with the formulation according to claim 1 before the plant is harvested.

13. A method, comprising:
storing, transporting, or both storing and transporting glyphosate and/or glyphosate monoisopropylammonium salt in form of the formulation according to claim 1.

* * * * *

UNITED STATES PATENT AND TRADEMARK OFFICE
CERTIFICATE OF CORRECTION

PATENT NO. : 10,278,385 B2
APPLICATION NO. : 13/720035
DATED : May 7, 2019
INVENTOR(S) : Stephan Hueffer et al.

It is certified that error appears in the above-identified patent and that said Letters Patent is hereby corrected as shown below:

In the Specification

Column 3, Line 60, delete "$(CH_3)_2CHNH(CH_3)^{2+}$," and insert -- $(CH_3)_2CHNH(CH_3)_2^+$, --

Column 5, Line 31, delete "$C_6$-$C_{20}$-" and insert -- $C_8$-$C_{20}$- --

Signed and Sealed this
Twenty-ninth Day of October, 2019

Andrei Iancu
*Director of the United States Patent and Trademark Office*